(12) United States Patent
Leonhardt et al.

(10) Patent No.: US 7,315,754 B2
(45) Date of Patent: Jan. 1, 2008

(54) ELECTRODE BELT

(75) Inventors: Steffen Leonhardt, Lübeck (DE);
Eckhard Teschner, Hamburg (DE);
Markus Hampe, Lübeck (DE);
Hans-Wilhelm Steen, Zarpen (DE);
Jianhua Li, Lübeck (DE); Karsten Hoffmann, Kasseedorf Griebel (DE);
Yvo Gärber, Lübeck (DE); Hans Matthiessen, Bad Schwartau (DE);
Rainer Degenhart, Stockelsdorf (DE);
Dieter Sahmkow, Lübeck (DE)

(73) Assignee: Dräger Medical AG & Co. KGaA, Lübeck (DE)

( * ) Notice: Subject to any disclaimer, the term of this patent is extended or adjusted under 35 U.S.C. 154(b) by 362 days.

(21) Appl. No.: 10/766,705

(22) Filed: Jan. 27, 2004

(65) Prior Publication Data
US 2004/0260167 A1    Dec. 23, 2004

(30) Foreign Application Priority Data
Apr. 8, 2003    (DE) ............................. 103 15 863

(51) Int. Cl.
*A61B 5/04* (2006.01)
(52) U.S. Cl. .................. 600/390; 600/386; 600/393
(58) Field of Classification Search ............... 600/372, 600/382, 384, 386, 390, 554, 547, 587, 595, 600/383
See application file for complete search history.

(56) References Cited

U.S. PATENT DOCUMENTS

| | | | | |
|---|---|---|---|---|
| 4,202,344 A | * | 5/1980 | Mills et al. | 600/382 |
| 4,308,872 A | * | 1/1982 | Watson et al. | 600/538 |
| 4,539,640 A | * | 9/1985 | Fry et al. | 600/547 |
| 4,681,118 A | * | 7/1987 | Asai et al. | 600/387 |
| 4,751,928 A | * | 6/1988 | Hallon et al. | 600/382 |
| 4,807,640 A | * | 2/1989 | Watson et al. | 600/534 |
| 5,191,886 A | * | 3/1993 | Paeth et al. | 600/382 |
| 5,313,952 A | * | 5/1994 | Hoch | 600/390 |
| 5,353,793 A | * | 10/1994 | Bornn | 600/386 |
| 5,782,238 A | * | 7/1998 | Beitler | 600/372 |
| 6,205,346 B1 | * | 3/2001 | Akiva | 600/388 |
| 6,353,396 B1 | * | 3/2002 | Atlas | 340/693.9 |
| 6,461,307 B1 | * | 10/2002 | Kristbjarnarson et al. | 600/534 |
| 2002/0097155 A1 | * | 7/2002 | Cassel et al. | 340/573.1 |
| 2004/0097839 A1 | * | 5/2004 | Epley | 600/595 |
| 2004/0236202 A1 | * | 11/2004 | Burton | 600/384 |

FOREIGN PATENT DOCUMENTS

EP    1 000 580 A1    5/2000

* cited by examiner

*Primary Examiner*—Max F. Hindenburg
*Assistant Examiner*—H. Q. Nguyen
(74) *Attorney, Agent, or Firm*—McGlew and Tuttle, P.C.

(57) ABSTRACT

An electrode belt for impedance tomography shall be improved such that it has a simple design and makes possible good contacting of the electrodes (2) with the body of the test subject to be examined. The electrode belt (1) has at least 16 electrodes (2) on an electrode holder or belt material (3), which is elastic at least in some sections. The belt formed of one or more belt material sections completely surrounds a test subject to be examined on the circumference of the body. Electrode feed lines (63) extend along the electrode holder (3). The electrode feed lines and are connected to a feed line (6) at least at one feed point (4) on the electrode holder (3).

31 Claims, 10 Drawing Sheets

ELECTRODE BELT

FIELD OF THE INVENTION

The present invention pertains to an electrode belt for electrical impedance tomography.

BACKGROUND OF THE INVENTION

Electrical impedance tomography (EIT) is a method in which a weak alternating electric current is introduced into the human body in order to measure the surface potentials at different points of the body. By rotating the sites at which the current is introduced around the body while measuring the surface potentials at the same time, a two-dimensional tomogram of the electrical impedance distribution in the body being examined can be determined by means of suitable mathematical reconstruction algorithms. A tomogram of the impedance distribution of the human body is of interest in medicine because the electrical impedance changes with both the content of air and the extracellular fluid content in the tissue. The ventilation of the lungs and the shifts in the blood and serum can thus be imaged and monitored in a regionally resolved manner.

To make it possible to carry out the measurement, the electrodes must be able to be arranged on the test subject's body in a simple manner. It is known that the electrodes may be arranged on a belt that can be placed around the test subject's body.

Such a belt, hereinafter called an electrode belt, has become known from EP 1 000 580 A1. An electrode holder with typically 16 electrodes is arranged on a test subject such that it fully encloses the circumference of the body. The electrode belt is connected via a feed line to an evaluating unit, in which the tomogram for the body section being examined is calculated.

SUMMARY OF THE INVENTION

The object of the present invention is to provide an electrode belt which has a simple design and makes possible the good contacting of the electrodes with the body of the test subject to be examined.

According to the invention, an electrode belt for electrical impedance tomography is provided with numerous electrodes (e.g, 16 or more). The electrodes are on a belt material, which is elastic at least in some sections and which fully surrounds a test subject to be examined over the circumference of the body. Electrode feed lines are provided, which extend along the belt material and are connected to a feed line (primary connection line) at least at one feed point (primary connection site).

The advantage of the present invention is essentially that at least some sections or even all of the electrode belt consist/consists of an elastic material and as a result, the electrode belt fits the body circumferences to be examined especially well. The suitable elastic materials are elastomers or also elastic fabrics, as they are known from bandages. Due to the elasticity of the belt material, the electrode belt is in contact with the test subject's upper body under a certain pretension, as a result of which a radial force component acts as a pressing force on the electrodes. The elastic belt material also makes possible a good adaptation to the respiratory movements of the test subject. Furthermore, it is advantageous that the electrode feed lines are integrated within the material of the belt, so that these can be united at a central point in order to establish the connection to an external feed line. In the event the electrode belt consists of an elastomer, the electrode feed lines may be incorporated in the elastomer material by vulcanization. The electrode feed lines are woven into the fabric material in the case of the elastic fabric.

According to an advantageous embodiment, two adjacent electrodes have shaped elements as a padding in the area of indentation of the body, e.g., in the chest area or in the area of the vertebral column, and a sufficient pressing pressure is achieved for the electrodes located there due to these shaped elements. The shaped elements may be structures made of an elastic material, which are integrated in the belt and model the shape of the concave indentations of the body and thus adapt themselves to the contour of the body especially well. It is also possible to fasten the shaped elements to the material of the belt on the outside in the area of the adjacent electrodes, so that the electrodes are pressed on by the shaped elements with the test subject in the recumbent position. The contact surfaces of the electrodes are designed such, e.g., in the form of a convex structure, that the pressing pressure does not lead to local skin damage as a consequence of the action of strong forces in a punctiform pattern.

The electrodes are expediently arranged at equally spaced locations from one another. Sixteen or 32 electrodes are present in a preferred embodiment, and a reference electrode, which is fastened at a predetermined distance from the other electrodes on the test subject's body, may also be present separately from the electrode belt.

In the case of certain image reconstruction algorithms, the image quality of the tomograms is markedly improved by the fact that the electrodes have an equidistant distribution at least in some sections.

The material of the belt advantageously consists of silicone, so that good intrinsic elasticity or stretchability is guaranteed by the material. Moreover, silicone is insensitive to the detergents and disinfectants usually used, so that the electrode belt has an especially long service life.

In a preferred embodiment, the electrode belt comprises individual belt segments, which are connected to one another by means of belt closures. The belt segments are designed such that they have an equal number of electrodes. There are 8 electrodes per segment in the case of a total of 16 electrodes and two belt segments.

In another preferred embodiment, the electrode belt comprises four belt segments with four electrodes each per segment. The splitting of the electrode belt into individual belt segments has the advantage that the number of electrode feed lines to be led in parallel per belt segment is reduced.

The belt closures are used to mechanically connect the individual belt segments. However, they may also establish an electrical contact with the adjacent belt segment, besides the mechanical connection. The feed line, which connects the electrode feed lines of the electrode belt with an evaluating unit, may be connected to the electrode belt in different ways. If the electrode belt comprises individual belt segments with the corresponding belt closures, individual feed lines may lead directly to the belt closures. However, it is also possible to separate the mechanical connection and the electrical connection from each other by laying the electrode feed lines of one belt segment in the direction of the center of the belt segment and connecting them to the feed line there. If the belt segment contains eight electrodes and the feed is in the middle of the belt segment, four electrodes each must be contacted starting from the feed point.

The advantage of an electrode belt split into belt segments with corresponding belt closures is that this design can be mounted easily and rapidly in unconscious patients. It is sufficient to turn the test subject on one side and then to place two belt segments connected with a belt closure, hanging down around the chest and the back, below the arm on the other side of the test subject. The test subject is then turned back on his back and the belt segments are connected with a second belt closure. By splitting the electrode belt into individual belt segments, the electrode belt can also be opened quickly in case of an emergency, e.g., in the case of imminent defibrillation. For example, the upper belt segment can be easily removed, e.g., by opening a belt closure, while the belt segment located under it remains under the test subject.

In another preferred embodiment, the shaped elements contain cavities, which are hermetically sealed against the environment and are filled with a medium, e.g., air, a liquid or a gel. This embodiment has the advantage that the force of gravity of the body being supported is distributed uniformly through the filled cavities and a more uniform pressing pressure of the different electrodes is achieved. An additional spring effect, which presses the electrodes better on the body, is achieved in the case of a gas filling due to the compressibility of the gas.

In another preferred embodiment, the shaped elements contain stabilizing inserts of a greater hardness, e.g., metal inserts, such as performed brass or aluminum plates. These inserts are integrated and cast in the electrode holder. The shaped elements are mechanically stabilized as a result of this, and, on the other hand, the inserts can act as spring elements, e.g., as a leaf spring, if designed accordingly, and are thus able to absorb forces and additionally press on the electrodes. It is also possible to preform the metal inserts such that they adapt themselves especially well to the indentations of the body in the region of the chest and the back.

The electrode belt advantageously comprises at least three strands (tubes), which extend in parallel and are connected section by section via cross struts (tube mounting piece), the electrodes being arranged directly at the cross struts. One of the strands is hollow from the inside and is designed to accommodate the electrode feed lines. If the shaped elements located under the electrodes are designed as cavities in the area of the cross struts, they can be put under pressure via the hollow strand, and a membrane, which is located on the top side of the cavities, bulges outwardly together with the electrodes in order to generate the necessary pressing pressure on the test subject's body. The pressure may be generated automatically with a pressure regulator or manually with bellows.

The electrode feed lines are advantageously folded in a zigzag-shaped or meandering pattern within the hollow strand in order to compensate the stretching of the electrode material. The electrode feed lines may be cast in an elastomer within the hollow strand.

According to an advantageous embodiment of an electrode belt comprising three strands extending in parallel, the shaped element is designed as a gel pad, which is clamped in between the two outer strands and the strand located in the middle. When the electrode belt is put in place, the gel pad is pressed by the two outer strands against the middle strand, as a result of which the contacting of the electrode is improved. The electrodes are located at the middle strand here. A gel pad is especially suitable on the back when the patient is in the recumbent position, because it adapts itself well to the body surface and prevents pressure sores from forming.

The electrode belt advantageously has a coding means, which is designed to generate a release signal for the signals transmitted via the feed line. The coding means may be designed as a plug-type connection on the feed line, a magnetic strip, a bar code strip or a transponder. If the coding means is designed as a plug type connection, the release signal is generated during plugging in. Individual contacts at the feed site of the electrode belt can be connected to one another for this purpose through wire bridges such hat a certain coding is recognized by the evaluating unit during the plugging in with the feed line. In the case of a magnetic strip, a bar code or a transponder, the evaluating unit contains a reader, with which the code can be detected and evaluated. It is also possible to integrate an EEPROM or a digital or analog electronic unit in the electrode belt. It can be recognized by evaluating the coding whether the correct electrode belt has been placed on the test subject and whether there is compatibility with the evaluating unit. The coding may advantageously contain manufacturer's data, the number of electrodes, the type of the belt and the size of the belt.

The feed line is advantageously designed for wireless communication between the electrode belt and the evaluating unit. A transmitter or a transmitter-receiver is located for this purpose in the vicinity of the electrode belt, or it is an integral part of the electrode belt, and a receiver or transmitter-receiver of a corresponding design is provided at the evaluating unit.

Exemplary embodiments of the present invention are shown in the drawings and will be explained in greater detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
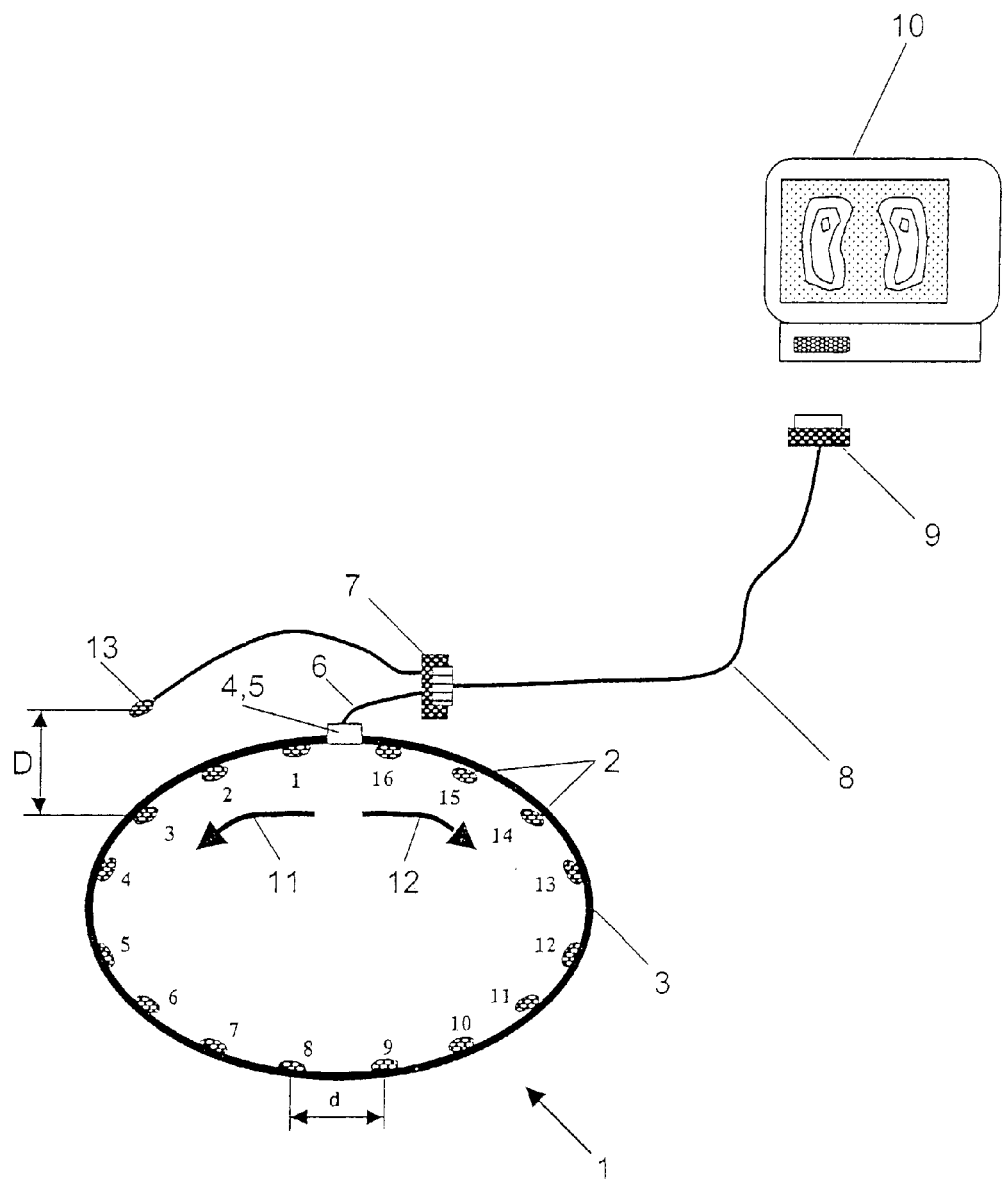
FIG. 1 is a schematic view of an electrode belt with an evaluating unit.

Referring to the drawings in particular, FIG. 1 schematically shows an electrode belt 1 for electrical impedance tomography with 16 electrodes 2 on an elastic electrode holder 3 made of silicone. For the sake of greater clarity, the 16 electrodes 2 are designated by the numbers 1-16. Electrode feed lines extend within the electrode holder 3. The electrode feed lines are not specifically shown in FIG. 1. The electrode feed lines are connected to a feed line (primary connection line) 6 at a feed point (primary connection site) 4, at which a belt closure 5 is located. Via a connection plug 7 with a connection cable 8 and a device plug 9, the feed line 6 is connected to an evaluating unit 10, in which all the calculations necessary for the impedance tomography are performed. The electrode belt 1 is placed around the upper body of a test subject, not specifically shown in FIG. 1. The electrode belt 1 can be opened at the belt closure 5. The belt closure 5 establishes both a mechanical connection and an electrical connection, because eight electrode feed lines each, indicated by arrows 11, 12, extend to the electrodes 2, starting from the belt closure 5. The electrodes are arranged at equal distance from each other. A reference electrode 13, which is likewise fastened to the test subject's body at the distance D relative to the electrode belt 1, is located above the electrode belt 1.

Figure 2:
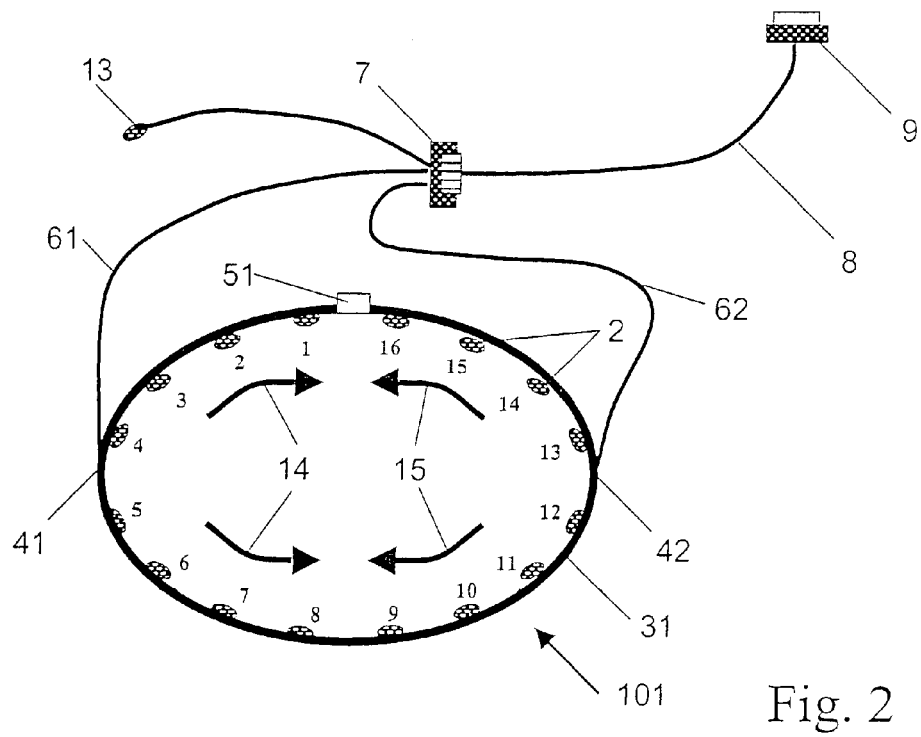
FIG. 2 is a schematic view of the electrode belt according to FIG. 1 with two feed lines arranged symmetrically.

FIG. 2 shows an alternative embodiment of an electrode belt 101, which has, unlike the electrode belt 1 according to FIG. 1, two feed lines 61, 62, which are connected separately by a belt closure 51 with an electrode holder 31. Starting from the feed points 41, 42 of the feed lines 61, 62, up to four electrode feed lines extend to the electrodes 2 along the arrows 14, 15. Identical components are designated by the same reference numbers as in FIG. 1.

Figure 3:
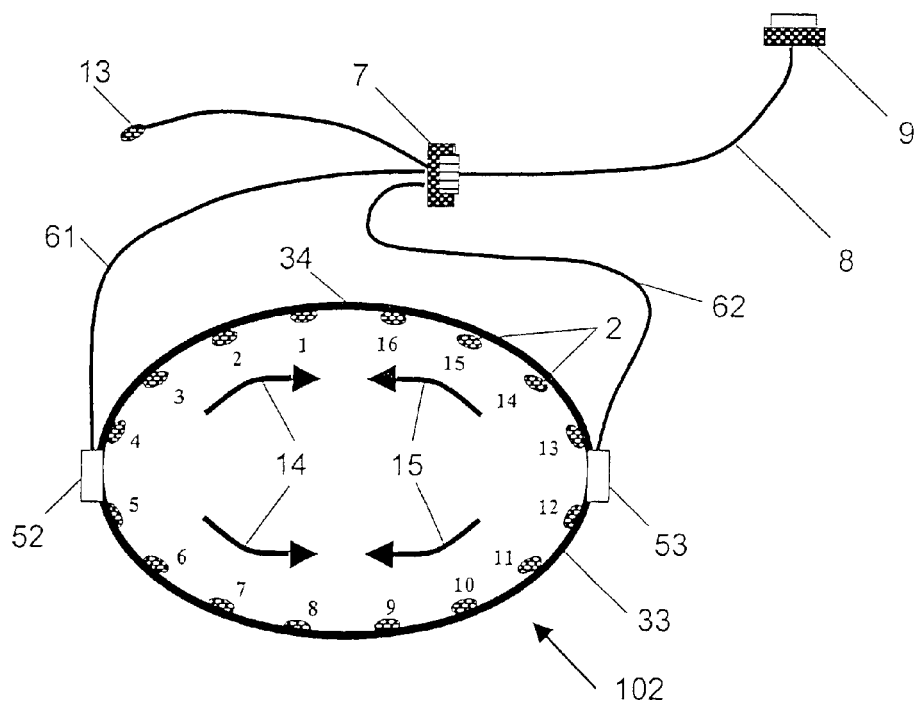
FIG. 3 is a schematic view of an electrode belt with two belt closures and symmetrical connection of the feed lines in the area of the belt closures.

Unlike in the embodiment according to FIG. 2, the feed lines 61, 62 are connected with a belt closure 52, 53 each in the electrode belt 102 according to FIG. 3. Because of the two belt closures 52, 53, the electrode belt 102 comprises a first belt segment 33 and a second belt segment 34, each with an equal number of electrodes 2.

Figure 4:
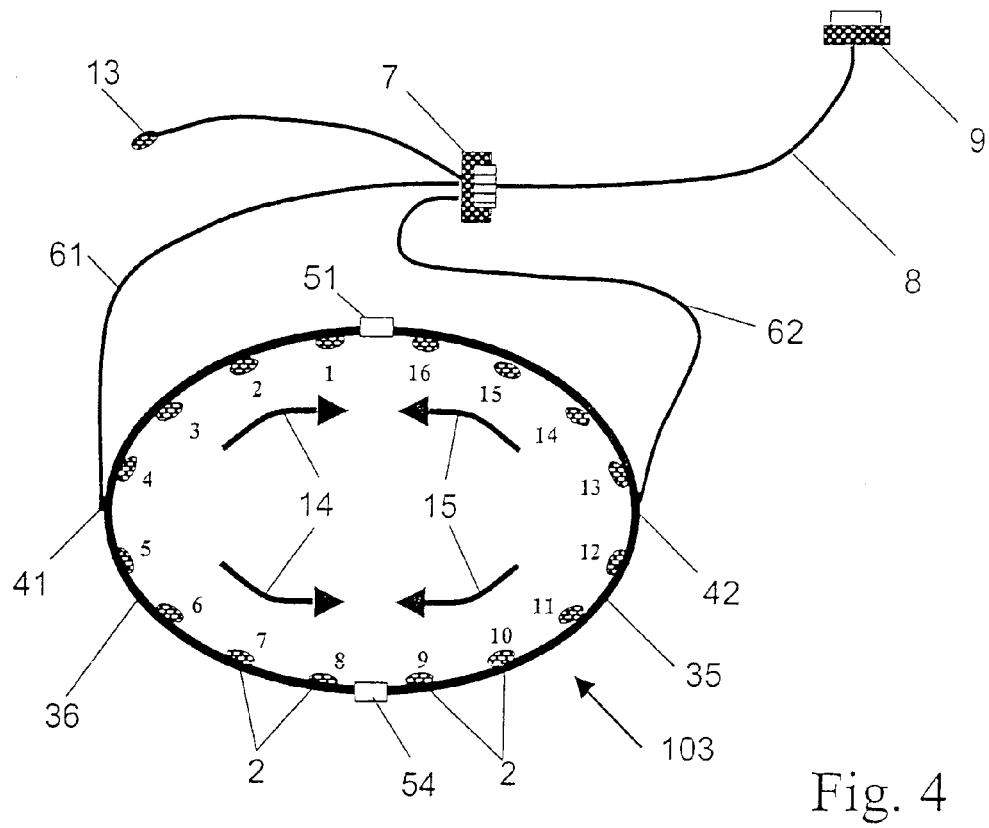
FIG. 4 is a schematic view of the electrode belt according to FIG. 2 with a second belt closure.

The electrode belt 103 according to FIG. 4 differs from the electrode belt 101 according to FIG. 2 by an additional belt closure 54, by which two belt segments 35, 36 with equal numbers of electrodes 2 are formed.

Figure 5:
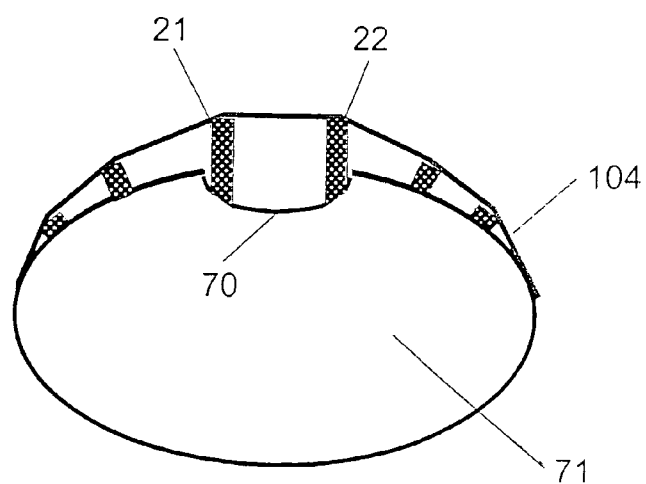
FIG. 5 is a schematic view of an electrode belt with electrodes bulging forward in the area of a depression of the body.

FIG. 5 schematically shows an electrode belt 104 lying on the sternal depression 70 of a test subject 71. To cover the sternal depression 70, two electrodes 21, 22 are provided, which are arranged adjacent to each other, bulge forward and lead to a radial force component when the electrode belt 104 is put in place.

Figure 6:
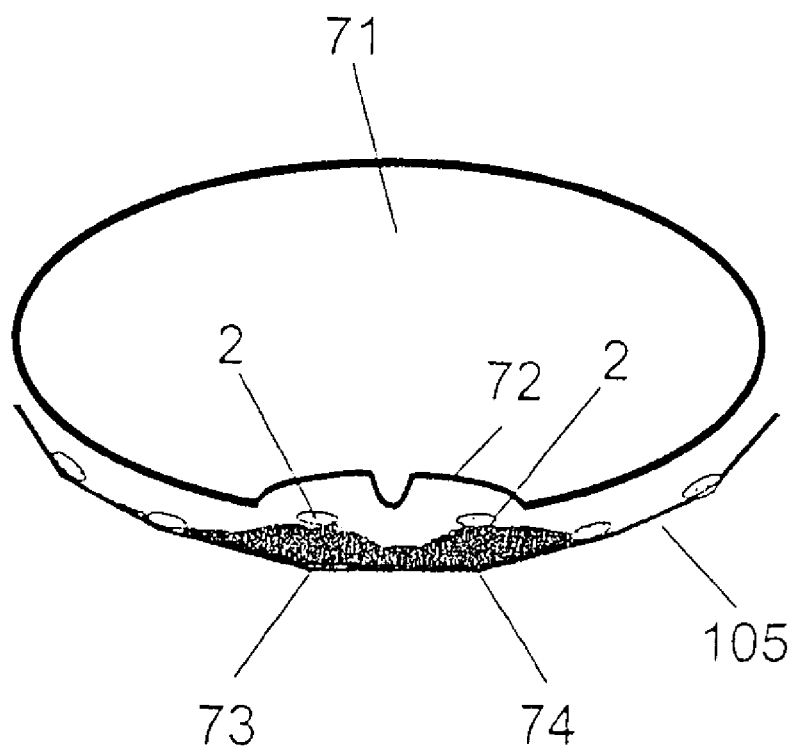
FIG. 6 is a schematic view of an electrode belt with shaped elements at two electrodes arranged adjacent to each other.

FIG. 6 illustrates the coverage of the spinal depression 72 of the test subject 71 with an electrode belt 105, in which shaped elements incorporated in the belt 105 in the form of bead-like projections 73, 74 are used as a padding for the electrodes 2.

Figure 7:
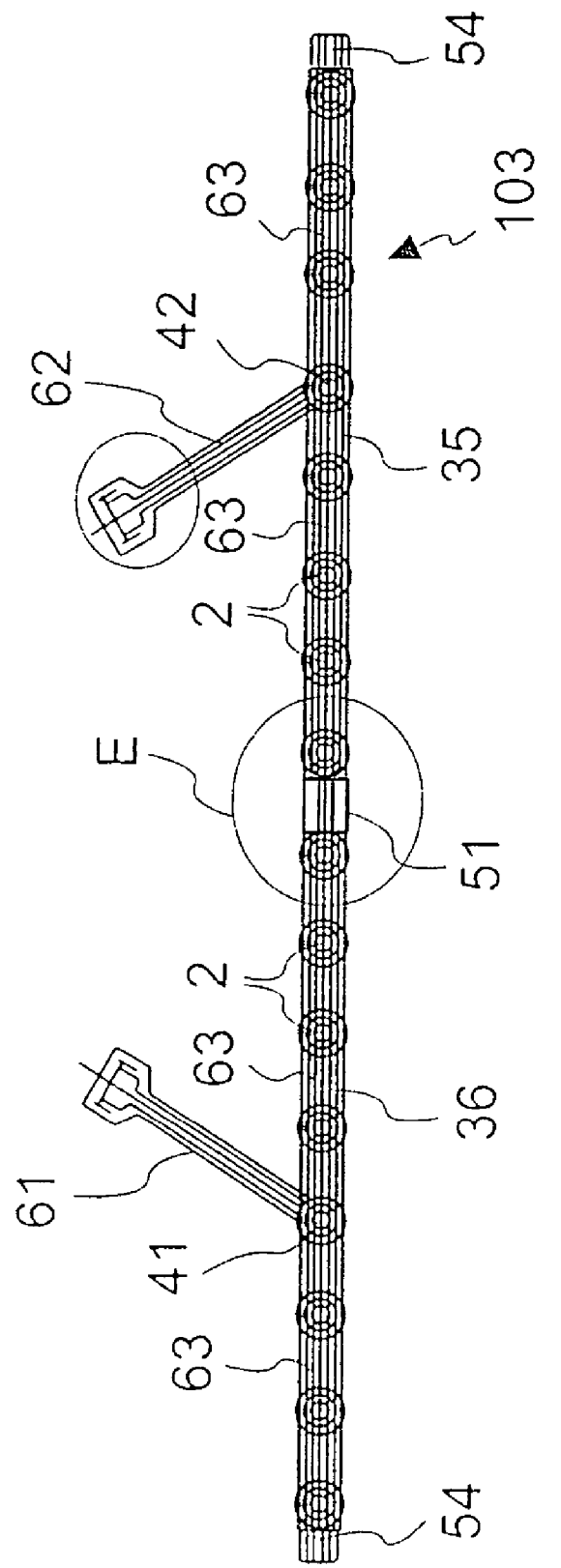
FIG. 7 is a top view of an electrode belt with two belt segments.

FIG. 7 shows a top view of the electrode belt 103 according to FIG. 4 with the belt segments 35, 36 and the belt closures 51, 54. The feed lines 61, 62 lead directly to the electrode feed lines 63, which, starting from the feed points 41, 42, extend directly to the electrodes 2.

Figure 8:
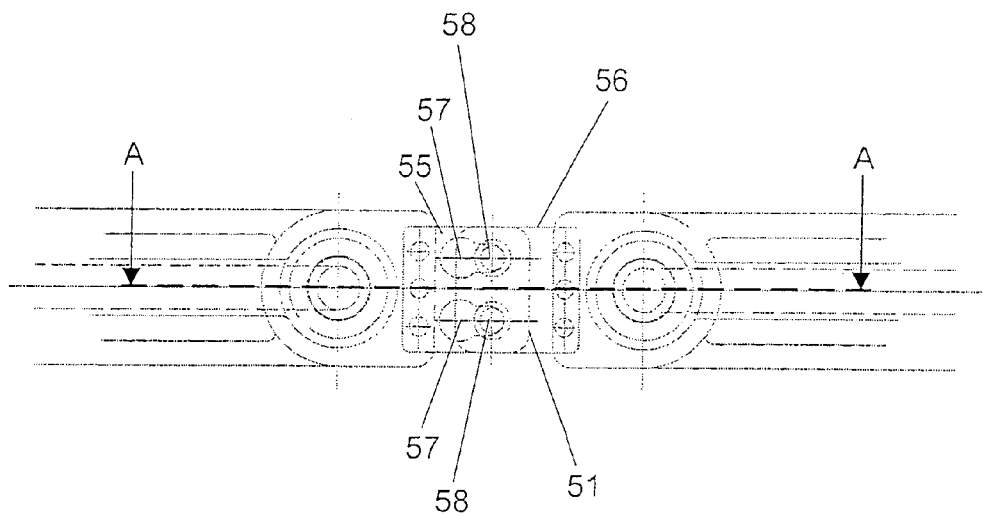
FIG. 8 is detail "E" from FIG. 7 with a belt closure.

FIG. 8 shows an enlarged detail E of the electrode belt 103 according to FIG. 7 with the belt closure 51. The belt closure 51 comprises two straps 55, 56, which can be displaced in relation to one another, wherein a first strap 55 has two tapering elongated holes 57, and a second strap 56 has rivets 58. The diameter of the rivets 58 is selected to be such that the rivets can be introduced into the elongated holes at the point where the elongated holes have the greatest internal diameter.

Figure 9:
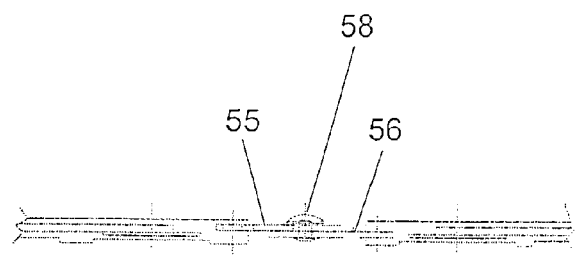
FIG. 9 is a sectional view along the section line A-A, corresponding to FIG. 8.

FIG. 9 shows a sectional view of the electrode belt 103 in the area of the belt closure 51 along the section line A-A.

Figure 10:
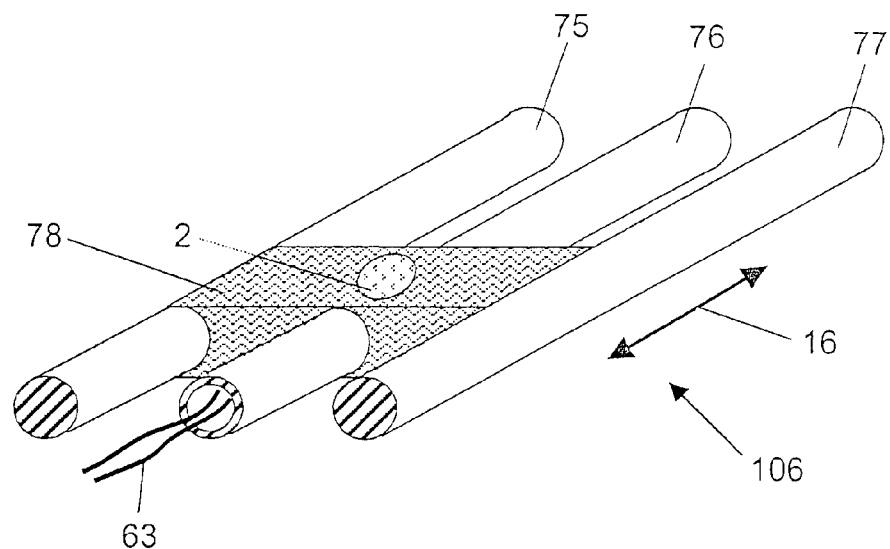
FIG. 10 is a perspective view of a detail of an electrode belt with three strands (tubes).

FIG. 10 shows a perspective view of an electrode belt 106, which comprises three strands (tubes) 75, 76, 77, which extend in parallel and are connected to one another section by section via cross struts (tube mounting piece) 78. The electrodes 2 are located in the middle on the cross struts 78. The two outer strands 75, 77 are made of an elastic solid material, whereas the middle strand 76, though also elastic, is hollow on the inside, so that it can accommodate electrode feed lines 63. The direction of stretching of the electrode belt 106 is illustrated by the double arrow 16.

Figure 11:
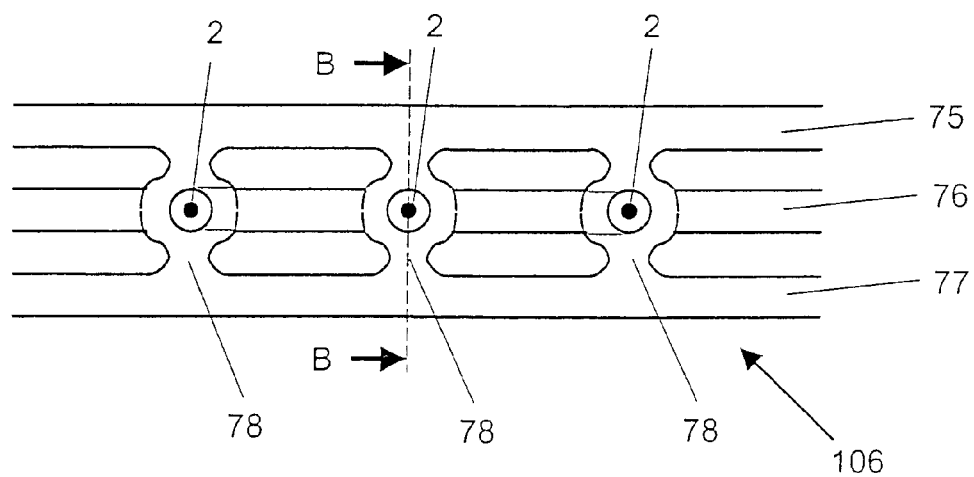
FIG. 11 is a top view of the electrode belt according to FIG. 10.

FIG. 11 shows a top view of the electrode belt 106 with cross struts 78, which are located next to each other and are arranged at equal distances from each other.

Figure 12:
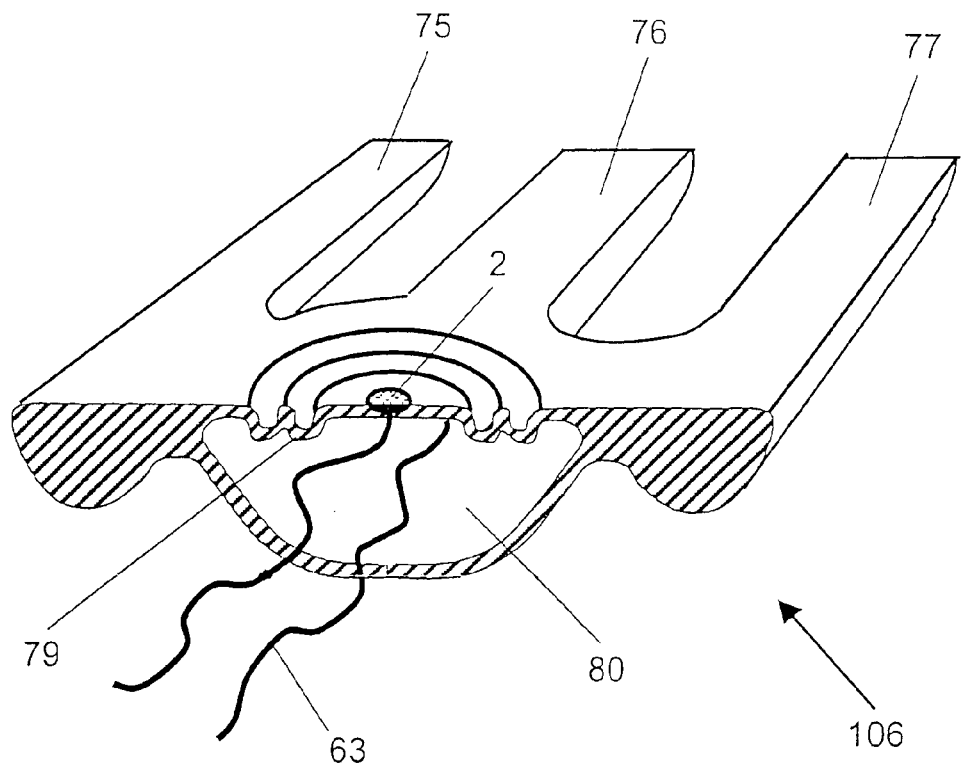
FIG. 12 is a sectional view along the section line B-B of the electrode belt according to FIG. 11.

FIG. 12 shows a sectional view of the electrode belt 106 according to FIG. 11 along a section line B-B. The electrode 2 is fastened to an elastic membrane 79 according to this embodiment. The elastic membrane 79 closes off a cavity 80. The individual cavities 80 can be put under pressure centrally via the middle strand 76, and the membranes 79 bulge outwardly. The pressing pressure of the electrodes 2 on the test subject's body can be affected by changing the pressure.

Figure 13:
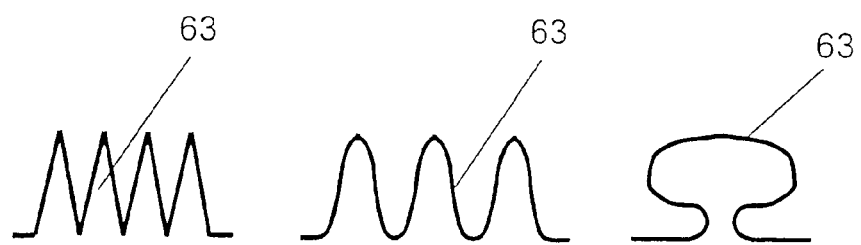
FIG. 13 is a view showing examples of folded electrode feed lines.

For strain relief of the electrode feed lines 63, the latter are folded within the middle strand 76 in a triangular, loop-like or meandering pattern, as can be determined from FIG. 13.

Figure 14:
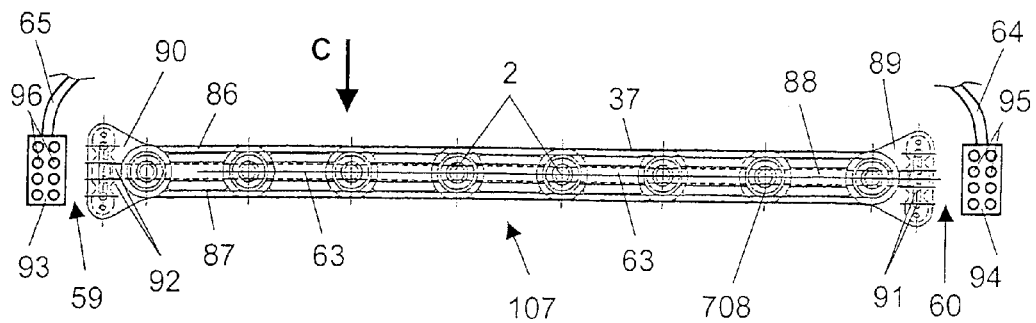
FIG. 14 is a top view of a belt segment of an electrode belt.

FIG. 14 shows an electrode belt 107, which comprises two belt segments 37 of identical design with eight electrodes 2 each. Only one belt segment 37 is shown in FIG. 14 for the sake of greater clarity.

The belt segment 37 has two outer strands 86, 87, which consist of an elastic solid material, and a middle, hollow strand 88, which is used to accommodate the electrode feed lines 63. Plug-in straps 89, 90, which act as feed points and have four plug type connections 91, 92 each for contacting four electrodes 2, are located at the ends of the belt segment 37. Thus, only a maximum of four electrode feed lines 63 need to be led in parallel within the hollow strand 88. Two plugs 93, 94 with feed lines 64, 65 for the electrodes 2 of the belt segment 37 have two rows located in parallel with contact pins 95, 96, which can be connected to the plug type connections 91, 92. The belt segment 37 is connected to the plugs 93, 94 both mechanically and electrically with the contact pins 95, 96 and the plug type connections 91, 92. A second belt segment 37, not shown in FIG. 14, is connected to the two free contact pins 95, 96 of the plugs 93, 94. The complete electrode belt 107 is obtained with two belt segments 37 and the plugs 93, 94. The plugs 93, 94, combined with plug type straps 89, 90, form the belt closures 59, 60 of the electrode belt 107.

Figure 15:
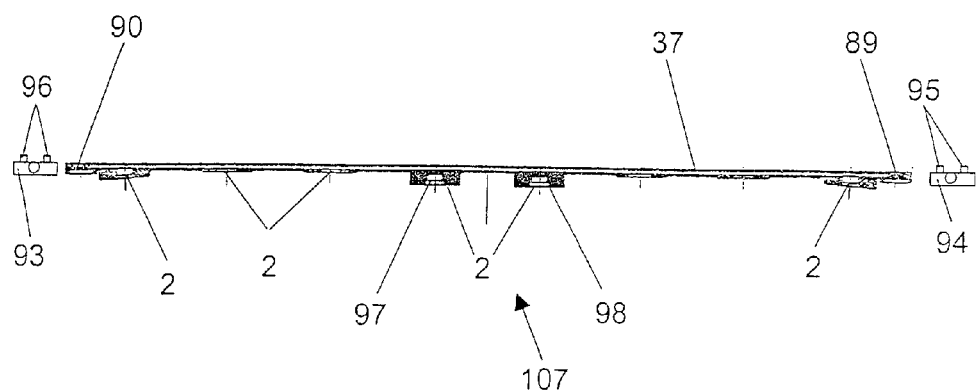
FIG. 15 is a side view of the belt segment according to FIG. 14 in the direction of view C.

FIG. 15 shows a side view of the electrode belt 107 in the direction of view C according to FIG. 14. Identical components are designated by the same reference numbers as in FIG. 14. The electrodes 2 are arranged at equal distances from each other on the belt segment 37. The electrodes 2 in the area of the middle of the belt have shaped elements 97, 98 as a padding in order to achieve good contacting in the chest or back regions.

Figure 16:
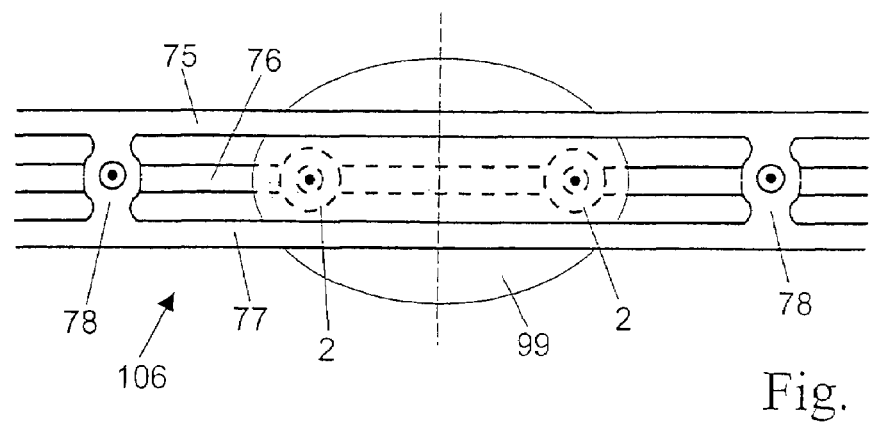
FIG. 16 is a schematic view of an alternative embodiment of the electrode belt according to FIG. 11 with a gel pad.

FIG. 16 shows an alternative embodiment of the electrode belt 106 according to FIG. 11. The electrodes 2 located adjacent to each other have as the shaped element a gel pad 99, which is clamped between the outer strands 75, 77 and the middle strand 76. FIG. 16 shows a top view of the electrode belt 106, in which the electrodes are concealed.

Figure 17:
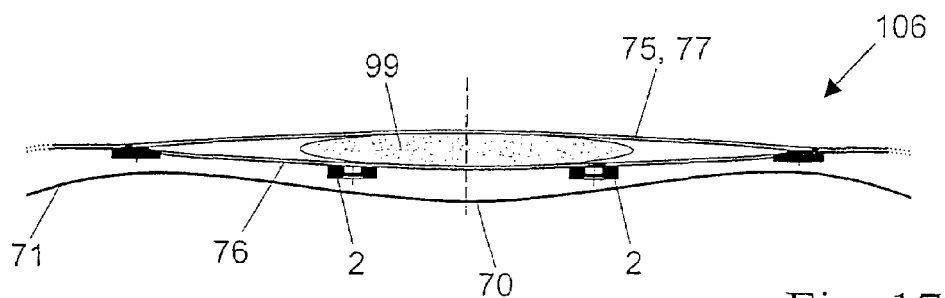
FIG. 17 is a side view of the electrode belt according to FIG. 16.

FIG. 17 shows a side view of the electrode belt 106 according to FIG. 16, which is in contact with the sternal depression 70 of the test subject 71. With the electrode belt 106 in place, a radial force is applied to the middle strand 76 by the outer strands 75, 77, as a result of which the electrodes 2 are pressed onto the sternal depression 70.

Figure 18:
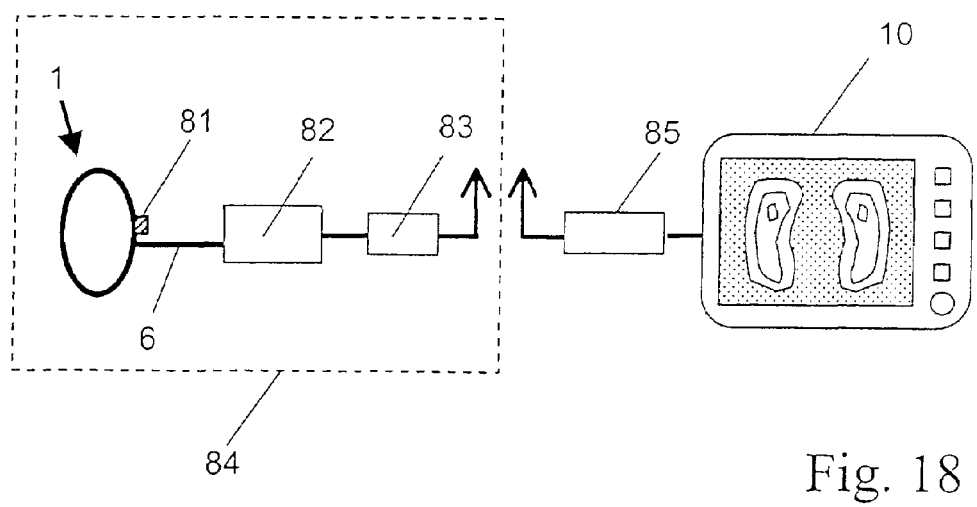
FIG. 18 is a schematic diagram showing an electrode belt and an evaluating unit with wireless communication.

FIG. 18 shows the concept of the wireless connection of an electrode belt 1 to an evaluating unit 10. In this embodiment, an analog and digital electronic unit 82 is accommodated together with a transmitter-receiver 83 in a housing 84 located near the test subject. The electronic components accommodated within the housing 84 are supplied with electricity by a separate power supply unit. The analog and digital electronic unit 82 is preferably designed for low energy consumption, as a result of which batteries can be used as the power supply. In an especially preferred embodiment, two sets of batteries are used, which can be removed one by one by means of a suitable mechanical or electromechanical change closure and recharged in an external charging station. It is thus not necessary to interrupt the measuring operation during the battery change. A transmitter-receiver 85, which receives the measured signals of the electrode belt 1, is likewise located in front of the evaluating unit 10. The wireless communication takes place via an infrared transmission link or a radio link with low output. Due to the wireless connection of the electrode belt 1 to the evaluating unit 10, the evaluating unit 10 can be placed in a site-independent manner from the test subject interface, and long cable connections, which are, moreover, prone to fault, are avoided. The electrode belt 1 has, moreover, a coding means 81 in the form of an EEPROM, which is activated when the feed line 6 is connected. It is thus possible to recognize whether the correct electrode belt 1 is connected to the evaluating unit 10.

While specific embodiments of the invention have been shown and described in detail to illustrate the application of the principles of the invention, it will be understood that the invention may be embodied otherwise without departing from such principles.

What is claimed is:

1. An electrode belt for electrical impedance tomography, the electrode belt comprising:
    a belt material;
    16 or more electrodes connected to said belt material, said belt material being elastic in some sections such that said belt material can be stretched from a non-stretched state to a stretched state, the electrode belt fully surrounding a test subject to be examined over the circumference of the body;
    electrode feed lines extending within one or more hollow elastic tubes, each electrode feed line having a defined length, said electrode feed lines being integrated within said belt material such that the entire length of each electrode feed line extends within said belt material, each electrode feed line having a length between electrodes that is greater than the length of said tubes between electrodes when the belt material is in a non-stretched state; and
    a feed line, said electrode feed line being connected to said feed line at one or more feed points along said belt material.

2. An electrode belt in accordance with claim 1, wherein said electrodes are arranged at equally spaced locations from one another on the belt material.

3. An electrode belt in accordance with claim 1, wherein said belt material and said electrode feed lines form plural belt segments with one or more of said electrodes arranged on individual belt segments.

4. An electrode belt in accordance with claim 1, wherein said feed points are arranged symmetrically in relation to one another with the belt material split into two sections of approximately equal size.

5. An electrode belt in accordance with claim 1, wherein said belt material comprises three or more tubes, which extend in parallel and are connected section by section via a tube mounting piece.

6. An electrode belt in accordance with claim 5, wherein said electrodes are arranged in the area of said tube mounting piece.

7. An electrode belt in accordance with claim 5, wherein one of said tubes is hollow and accommodates said electrode feed lines.

8. An electrode belt in accordance with claim 5, further comprising: shaped elements provided as padding for two or more adjacent said electrodes for covering a sternal or spinal depression of a test subject wherein a gel pad located between outer tubes and a middle tube is provided as said shaped element.

9. An electrode belt for electrical impedance tomography, the electrode belt comprising:
    an electrode holder having a defined length for surrounding the body of a test subject, said electrode holder being composed of a stretch material, said electrode holder comprising one or more hollow elastic tubes;
    16 or more electrodes, said 16 or more electrodes being located on said electrode holder, each electrode being positioned along said electrode holder at a spaced location from an adjacent electrode to define an electrode holder portion;
    electrode feed lines extending within said one or more hollow elastic tubes, each electrode feed line having a defined length, said electrode feed length extending within said stretch material, said stretch material surrounding the length of said electrode feed line, each electrode feed line having a length that is greater than the length of said electrode holder portion when the electrode holder stretch material is in a non-stretched state; and
    an external feed line, said external feed line being connected to said electrode feed lines at one or more connection sites on said electrode holder.

10. An electrode belt for electrical impedance tomography, the electrode belt comprising:
    an electrode holding belt, said electrode holding belt comprising one ore more elastic tubes;
    16 or more electrodes, said 16 or more electrodes being positioned on said electrode holding belt;
    electrode feed lines extending within the one or more hollow elastic tubes, said electrode feed lines having a length between electrodes that is greater than a length of said elastic tubes in a non stretched state; and a primary connection line, said primary connection line being joined to said electrode feed lines at one or more primary connection sites on said electrode holding belt.

11. An electrode belt in accordance with claim 10, wherein said belt comprises three or more tubes, which extend in parallel and are connected section by section via a tube mounting piece.

12. An electrode belt in accordance with claim 11, further comprising: shaped elements provided as padding for two or more adjacent said electrodes for covering a sternal or spinal depression of a test subject wherein a gel pad located between outer tubes and a middle tube is provided as said shaped element.

13. An electrode belt in accordance with claim 11, wherein said electrodes are arranged in the area of said tube mounting piece.

14. An electrode belt in accordance with claim 10, wherein said electrode holding belt and said electrode feed lines form plural belt segments with one or more of said electrodes arranged on individual belt segments.

15. An electrode belt in accordance with claim 10, wherein said electrodes are arranged at equally spaced locations from one another on said electrode holding belt.

16. An electrode belt in accordance with claim 10, further comprising: shaped elements provided as padding for two adjacent said electrodes for covering a sternal or spinal depression of a test subject.

17. An electrode belt in accordance with claim 10, wherein silicone is the material used for said electrode holding belt.

18. An electrode belt in accordance with claim 10, further comprising a belt closure provided between two adjacent electrodes.

19. An electrode belt in accordance with claim 14, further comprising belt closures wherein each of said belt segments is provided with one of said belt closures.

20. An electrode belt in accordance with claim 14, wherein said electrodes are arranged at equal distances from each other within said belt segments.

21. An electrode belt in accordance with claim 19, wherein said feed points for electrode feed lines are provided on each of said belt closures.

22. An electrode belt in accordance with claim 16, wherein said shaped elements are designed as one or more of said electrodes bulging forward.

23. An electrode belt in accordance with claim 16, wherein the shaped elements are projections.

24. An electrode belt in accordance with claim 16, wherein the shaped elements comprising cavities, which can be filled with a medium and are closed with an elastic membrane.

25. An electrode belt in accordance with claim 24, wherein liquids, gels or gases are provided as said medium.

26. An electrode belt in accordance with claim 13, wherein said electrode feed lines are disposed or folded in a triangular, meandering or loop-like pattern.

27. An electrode belt in accordance with claim 10, wherein said electrode belt has a coding means for providing information relating to the belt.

28. An electrode belt in accordance with claim 27, wherein said coding means is designed as a plug type connection on a feed line, a magnetic strip, a bar code strip, an EEPROM, a transponder or a digital/analog electronic unit.

29. An electrode belt in accordance with claim 10, further comprising:

an evaluating unit; and wireless means for wireless communication between said electrode belt and said evaluating unit.

30. An electrode belt in accordance with claim 29, wherein said wireless means is connected in one assembly unit with said electrode belt.

31. An electrode belt for electrical impedance tomography, the electrode belt comprising:

a belt material, said belt material comprising three or more tubes, which extend in parallel and are connected section by section via a tube mounting piece;

16 or more electrodes on said belt material, said belt material being elastic in some sections, the electrode belt fully surrounding a test subject to be examined over the circumference of the body;

electrode feed lines, said electrode feed lines being integrated within said tubes;

shaped elements provided as padding for two or more adjacent said electrodes for covering a sternal or spinal depression of the test subject, wherein a gel pad located between outer tubes and a middle tube is provided as said shaped element; and a feed line, said electrode feed line being connected to said feed line at one or more feed points along said belt material, each electrode feed line having a length between electrodes that is greater than the length of said tubes between electrodes when the belt material is in a non-stretched state.

* * * * *